Figure 1:
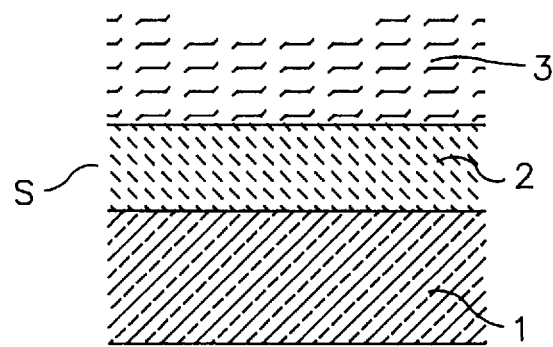

United States Patent [19]
Wolfbeis

[11] Patent Number: 5,853,669
[45] Date of Patent: Dec. 29, 1998

[54] SENSOR MEMBRANE FOR INDICATING THE PH OF A SAMPLE, THE FABRICATION AND USE THEREOF

[75] Inventor: Otto S. Wolfbeis, Graz, Austria

[73] Assignee: Merck Patent Gesellschaft mit Beschrankter Haftung, Germany

[21] Appl. No.: 588,767

[22] Filed: Jan. 19, 1996

Related U.S. Application Data

[63] Continuation of Ser. No. 211,272, Mar. 29, 1994, abandoned.

[30]     Foreign Application Priority Data

Sep. 30, 1991 [AT]   Austria ...................................... 91-1961

[51] Int. Cl.$^6$ ........................ G01N 21/29; G01N 21/00; G01N 33/48; G01N 21/75
[52] U.S. Cl. .......................... 422/82.05; 422/55; 422/56; 422/57; 422/58; 436/63; 436/164; 436/166; 436/169; 436/805; 436/807
[58] Field of Search ........................... 128/630; 204/400; 436/164, 63, 166, 169, 805, 807; 422/55, 56, 57, 58

[56]     References Cited

U.S. PATENT DOCUMENTS 4,200,110   4/1980   Peterson et al. ........................ 128/634
4,965,087   10/1990   Wolfbeis et al. ............................ 427/2

OTHER PUBLICATIONS

Zhujun et al., "Poly(vinyl alcohol) as a Substrate for Indicator Immobilization for Fiber–Optic Chemical Sensors", *Analytical Chemistry*, vol. 61, No. 3 (Feb. 1, 1989), pp. 202–205.
Leiner et al., "Fiber Optic pH Sensors", *Fiber Optic Chemical Sensors and Biosensors*, vol. 1, Chapter 8 (1991), pp. 359–369.

*Primary Examiner*—Susan A. Loring
*Attorney, Agent, or Firm*—Millen, White, Zelano & Branigan, P.C.

[57]     ABSTRACT

For the purpose of reversible optical indication of the pH of a sample, a hydrophilic accommodating layer is disposed on a hydrophobic mechanically stable support element, which layer contains the indicator dye proper in an immobilized form. This provides a sensor membrane which can be fabricated in a simple manner and is cost-effective, which has a rapid response time and can also be fabricated as a mass product to be used only once.

10 Claims, 5 Drawing Sheets

SENSOR MEMBRANE FOR INDICATING THE PH OF A SAMPLE, THE FABRICATION AND USE THEREOF

This is a continuation, of the application Ser. No. 08/211, 272, filed Mar. 29, 1994 now abandoned.

The invention relates to a sensor membrane for the reversible optical indication of the pH of a sample, having a mechanically stable support element and an indicator dye layer disposed thereon. The invention further relates to a process for fabricating a sensor membrane for reversible optical indication of the pH of a sample, in which a layer comprising indicator dye is applied onto a mechanically stable support element. Finally, the invention also relates to the use of a sensor membrane of this type.

The optical measurement of the pH goes back to the finding that certain dyes, (such as, for example, litmus) react to the pH of a sample by changing their color and are thus able to indicate the pH of a sample. A selection of suitable dyes (indicators), together with the pH ranges within which they change color, is found, for example, in "Indicators", E. Bishop, Pergamon Press, 1972, chapter 3.

The first pH-sensitive strip materials were obtained by immersing a paper strip in a dye solution. The dye in color strips of this type is bound to the support by absorption. This has the drawback that the dye can be washed out by the sample, which makes such strips unsuitable for sensor-type (on-line) applications, as the optically scanned signal becomes increasingly weaker owing to washing out rather than owing to changes of the pH.

By means of chemical or physical immobilization of dyes washing out can be prevented. Immobilized pH-sensitive materials are therefore suitable for the continuous measurement of the pH. Processes for immobilizing pH indicators on solid supports (cellulose, agarose, poly(methyl acrylates), polyacrylamide, glass) are known from the prior art.

Methods and configurations for the continuous optical measurement of pH have been described in the literature. In European Patent 137,157 and U.S. Pat. No. 4,548,907 a pH sensor is described in which a pH indicator is immobilized onto a membrane and the changes in the fluorescence intensity according to pH are polled via a light pipe. A similarly fiber-optical configuration based on the principle of the reflection of light was described in U.S. Pat. Nos. 4,200,110 and 4,476,870. U.S. Pat. No. 4,166,804 likewise describes the immobilization of a dye and the use of the material thus produced for the continuous measurement of pH. U.S. Pat. No. 4,716,118 describes the immobilization of pH indicators as well as the measurement of the ionic strength of a solution via an accurate measurement of the pH. A similar method described in U.S. Pat. No. 4,376,827 enables the determination of the ionic strength with the aid of a test strip.

Further optical pH measurement methods are found in U.S. Pat. Nos. 4,473,650, 4,318,709 and 4,532,216. U.S. Pat. No. 4,568,518 describes a pH-sensitive fluorescing cellulose membrane with an indicator which is bound to an inter-penetrating network of poly(ethyleneimine). Finally, EP-A 126,600 describes an optical sensor in which the indicator is bound to ion exchanger spherules, while U.S. Pat. No. 4,321,057 quite generally describes a fiber-optic sensor with a pH-sensitive material which is not specified in any detail.

Anal. Chem. 58, 2496 (1986) describes the use of a commercially available pH indicator strip as a sensor in an automated analysis system. The paper strip is introduced into a flow cell and its color changes are scanned via a light pipe. The response time of this sensor is from 3 to 15 minutes, as can be seen from the FIGS. 5B and 7B of the cited article. The response speed in this case decreases considerably with decreasing buffer capacity. Response times as long as this are unsuitable in practice, and the authors therefore use the so-called "transient technique", i.e. instead of waiting for a constant signal, the measurement is carried out after a defined time interval.

Anal. Chem. 47, 348 (1975) describes reusable pH indicators bound to glass, while Anal. Chem. 60. 404 (1988) describes an optical pH sensor which was obtained by chemical modification of a porous polymer film. Both types of sensors are very laborious to fabricate, require considerable experience in the field of immobilization chemistry and are difficult to fabricate reproducibly, especially if glass is used as the support.

A drawback of all these sensors is the fact, as quoted above, that the response times, from 1.0 to 20 minutes, are relatively long, which is a considerable drawback compared to the short response times of pH electrodes. These electrodes, in contrast to the membranes discussed herein, cannot be used on site in as simple a manner as a test strip, nor can they be designed as simple and inexpensive disposable components. More-over, pH electrodes function only in strongly buffered systems.

Anal Chem. 59, 437 (1987) discloses how to apply the dye and the support as an extremely thin film onto the light pipe, in order to shorten the response times. Similar information is disclosed by Anal. Sci. 3, 7 (1987).

This process suffers from one or more of the following drawbacks: they are [sic] complicated, produce [sic] poorly reproducible results and, because of the small amount of dye present in the layer which is a few nm thick, produce [sic] only a very weak signal, so that only poor signal resolution is achieved. The commercially available indicator papers, on the other hand, suffer from the drawback that they are unsuitable in practice for unbuffered solutions, as the relatively large amount of immobilized dye itself represents a considerable buffer capacity. Finally, said sensor membranes are also opaque, so that they can be measured only in reflectance rather than in absorption (in transmitted light). The only exception to this is found in the methods for immobilization on glass, by which, according to the method cited above from Anal. Chem. 47, 348 (1975) a transparent material is obtained which, however, is unsuitable for practical applications owing to the fragility glass sensors and the difficulty of mass-producing them.

The object of the present invention is to improve a sensor membrane of the type mentioned in the preamble and a process for fabricating a sensor membrane of this type so as to overcome the said drawbacks and, in particular, so as to enable a simple fabrication or even mass production of sensor membranes which are inexpensive and thus suitable as an expendable sensor and which have a short response time, the aim being also to provide the hitherto unavailable possibility of using such sensor membranes in unbuffered or weakly buffered systems.

The present invention relates to a sensor membrane for the reversible optical indication of the pH of a sample, having a mechanically stable support element and an indicator dye layer disposed thereon, characterized in that a hydrophilic accommodating layer is disposed on at least one side of the support element, which layer contains the indicator dye in an immobilized form. The corresponding process for fabricating the sensor membrane, according to the invention, is characterized in that a hydrophilic accommodating layer is applied onto the support element, into which layer the indicator dye is introduced and immobilized. This can be done prior to or following the application of the accommodating layer onto the support element.

According to the invention the sensor membrane is therefore formed in such a way that a hydrophilic second accommodating layer is attached onto the support element in a conventionally only very thin layer from 0.1 to 20 μm, preferably from 0.1 to 0.5 μm, which layer carries or contains the indicator dye proper. The support element therefore serves only as a base for mechanical reinforcement, while the sensor film proper is applied in an extremely thin hydrophilic layer.

According to an advantageous further development of the invention, the accommodating layer comprises cellulose, gelatine, hydrogel, hydrophilic polyvinyl alcohols or mixtures of these substances. The support element, which has the accommodating layer together with the indicator dye, comprises hydrophobic, optically transparent material, preferably from the group: polyesters of the phthalate type, polycarbonates, polyvinyl chlorides, polyamides, silicones, crosslinked polyacrylamides or polyvinyl alcohols. Particularly preferred materials for the support element are polyesters of the phthalate type, and for the hydrophilic accommodating layer, cellulose.

Onto the hydrophilic thin top coat, the corresponding pH indicator dyes can then be immobilized in a conventional manner. Alternatively, the dye indicator can first be immobilized onto the thin hydrophilic membrane, whereupon the latter is applied to the hydrophobic support.

Conventionally, reactive indicators are used, i.e. those which, in addition to the pH-sensitive absorption, also have a chemical function (R) by means of which chemical bonding to the hydrophobic support layer becomes possible. Dyes (indicators) bound covalently in this manner can no longer be washed out.

Typical chemical structures of reactive indicators are, for example, the following:

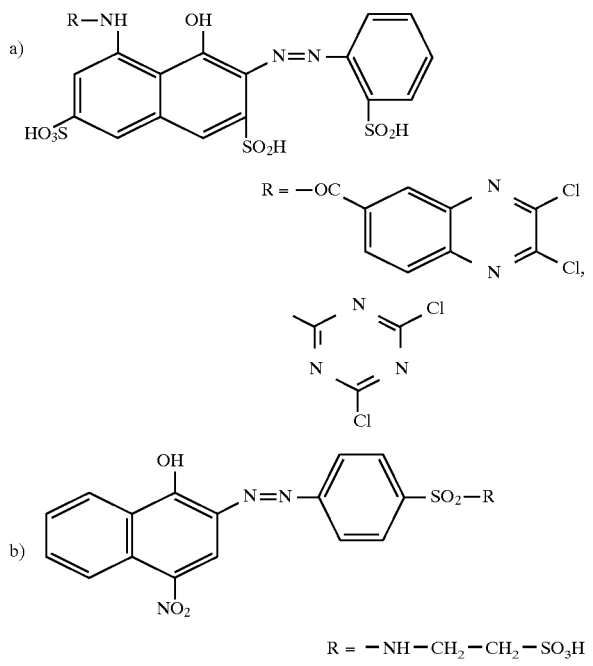

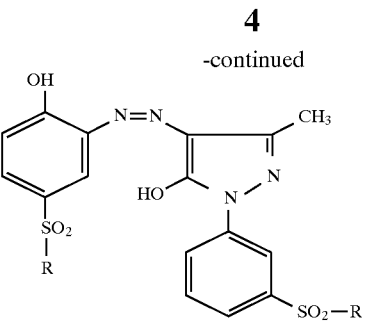

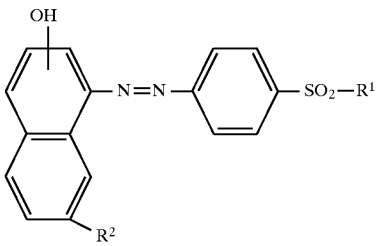

$R^1 = -CH_2-CH_2-O-SO_3H$
$R^2 = H, -SO_3H$
$R^3 = -NO_2, -SO_3H$

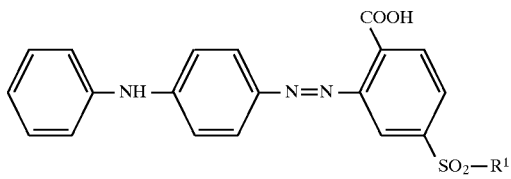

The sensor layers thus obtained, in contrast to prior art layers, are optically perfectly transparent and are thus readily usable for photometric absorption measurements. Moreover, they can be fabricated in large quantities at little cost, since coating and immobilization of the dye can be carried out virtually in on-line operation. Finally, the membranes thus obtained, because of the thin indicator layer, have a very low buffer capacity which makes them very suitable for the purpose of measuring unbuffered solutions (for example when detecting acid rain) and a rapid response time, since the diffusion of the protons through the thin hydrophilic indicator layer can take place much more rapidly than in previously known relatively thick sensor layers.

In a refinement of the membrane the latter, as previously mentioned, may also be coated on both sides, especially if evaluation is carried out by absorption measurements rather than by reflectance or fluorescence measurements, and if the sample can have access on both sides.

The evaluation of the color intensity of the sensor membrane can also be carried out with the aid of fiber-optic or intergrated [sic] optical methods. In this case the hydrophilic thin layer can be applied directly onto hydrophobic optical waveguide material. Relevant configurations are described, for example, in volume 1 of the book "Fiber Optic Chemical Sensors and Biosensors" by O. S. Wolfbeis, CRC Press, Boca Raton, Fla., 1991, chapters 2 and 3.

In an alternative refinement of the membranes according to the invention, the latter can also be used as reference elements. To this end, part of the membrane surface is covered with a gas- or proton-impermeable material or else is not brought into contact with the sample. An area is thus obtained whose color intensity is not altered by the sample and which, in the case of photometric evaluation, can serve as a reference element whose signal represents a reference value.

The pH sensors according to the invention can be used not only to measure pH but, if suitably refined, especially by covering with gas-permeable layers, can serve for the optical detection of acidic or alkaline gases as described, for example, in volume 2, chapter 11 of the book cited above. Finally, such sensors can also be used as transducer elements for biochemical reactions in which the pH changes. This too has been described before per se, for example in Anal. Chem. 60, 433 (1988) for the determination of penicillin.

Figure 6:
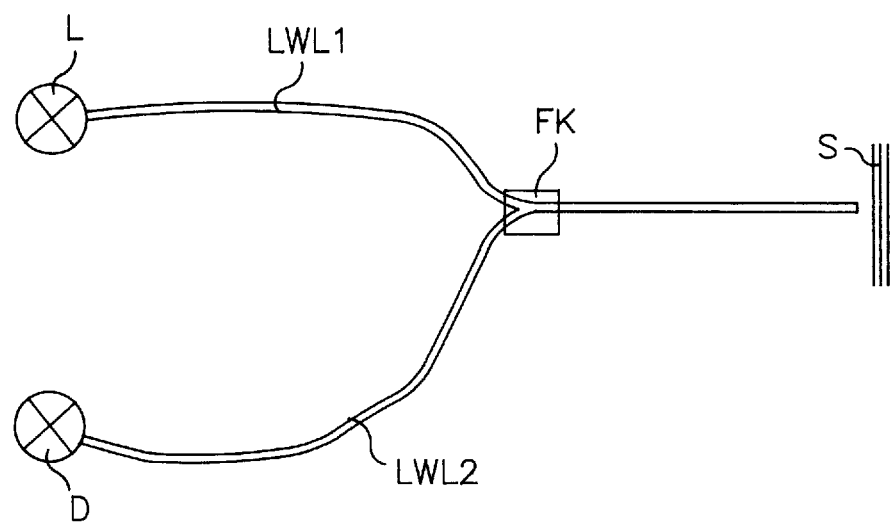
Figure 2:
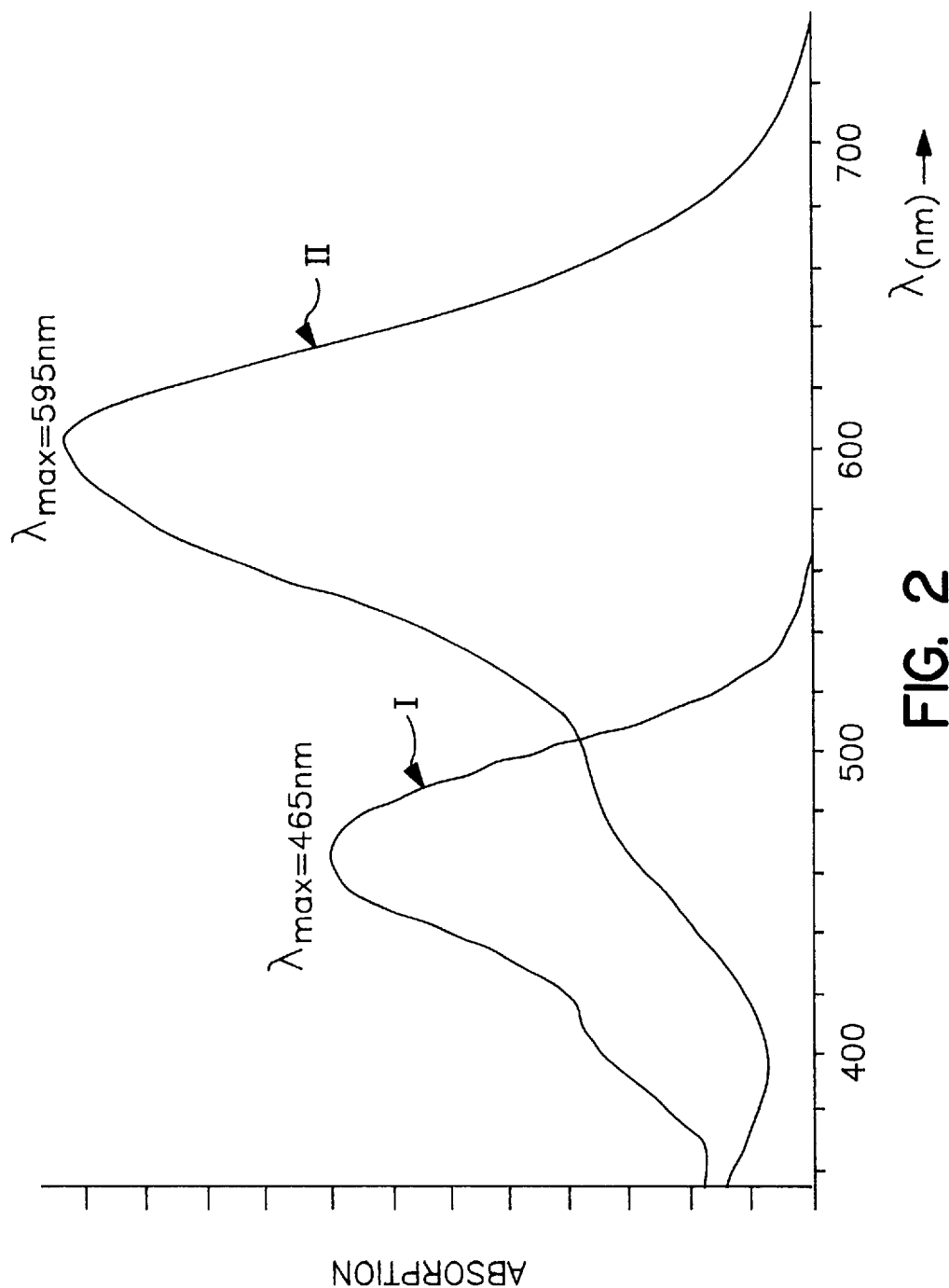
Figure 3:
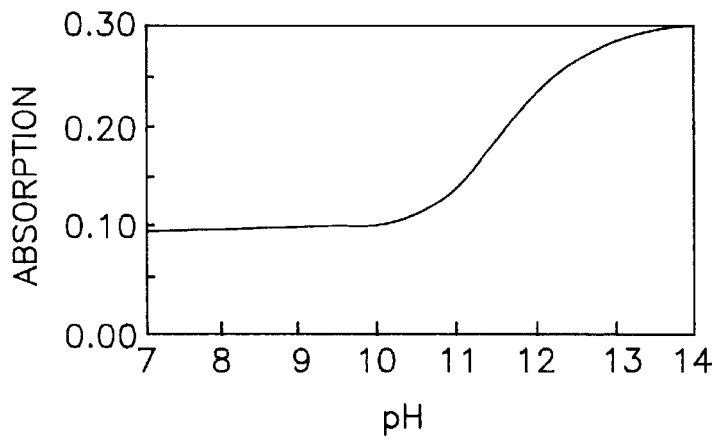
Figure 4:
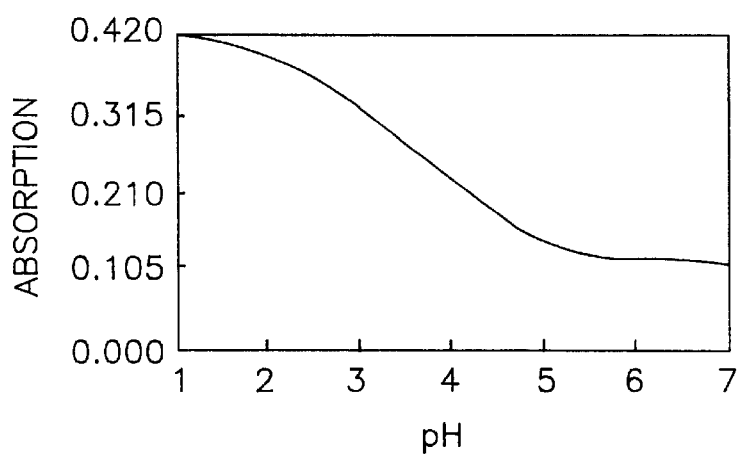
Figure 5:
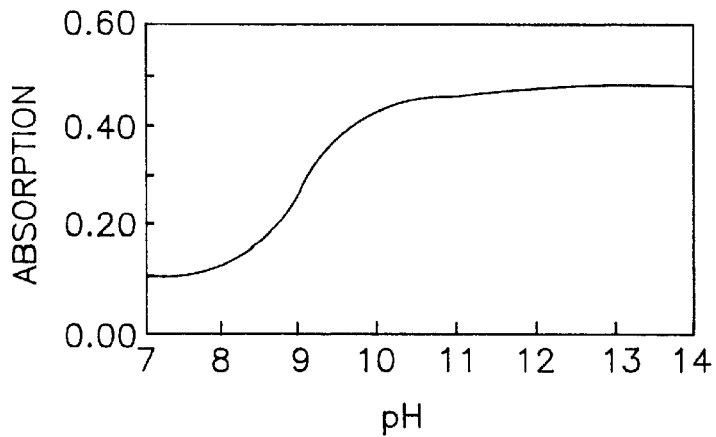
Figure 7:
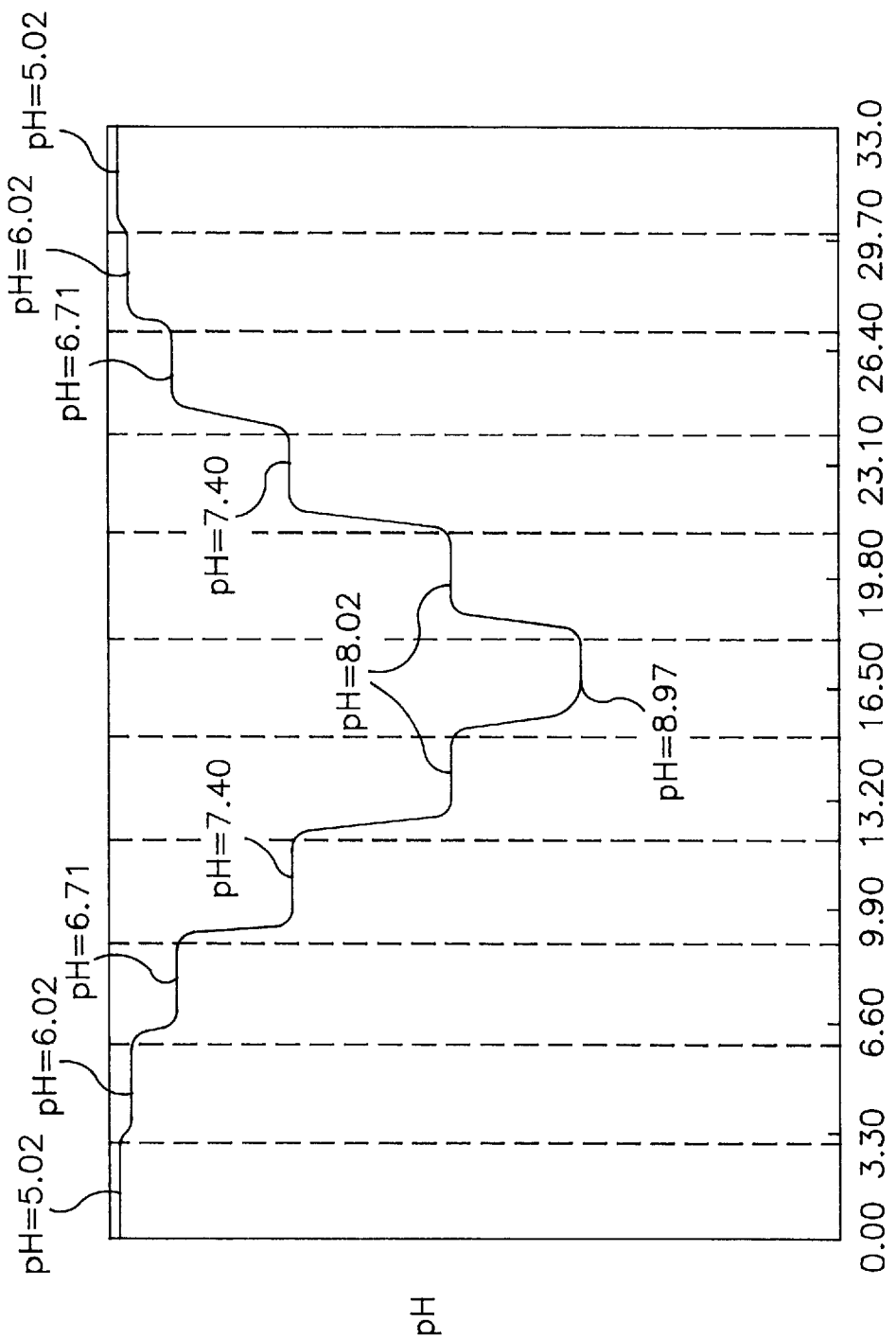
Figure 8:
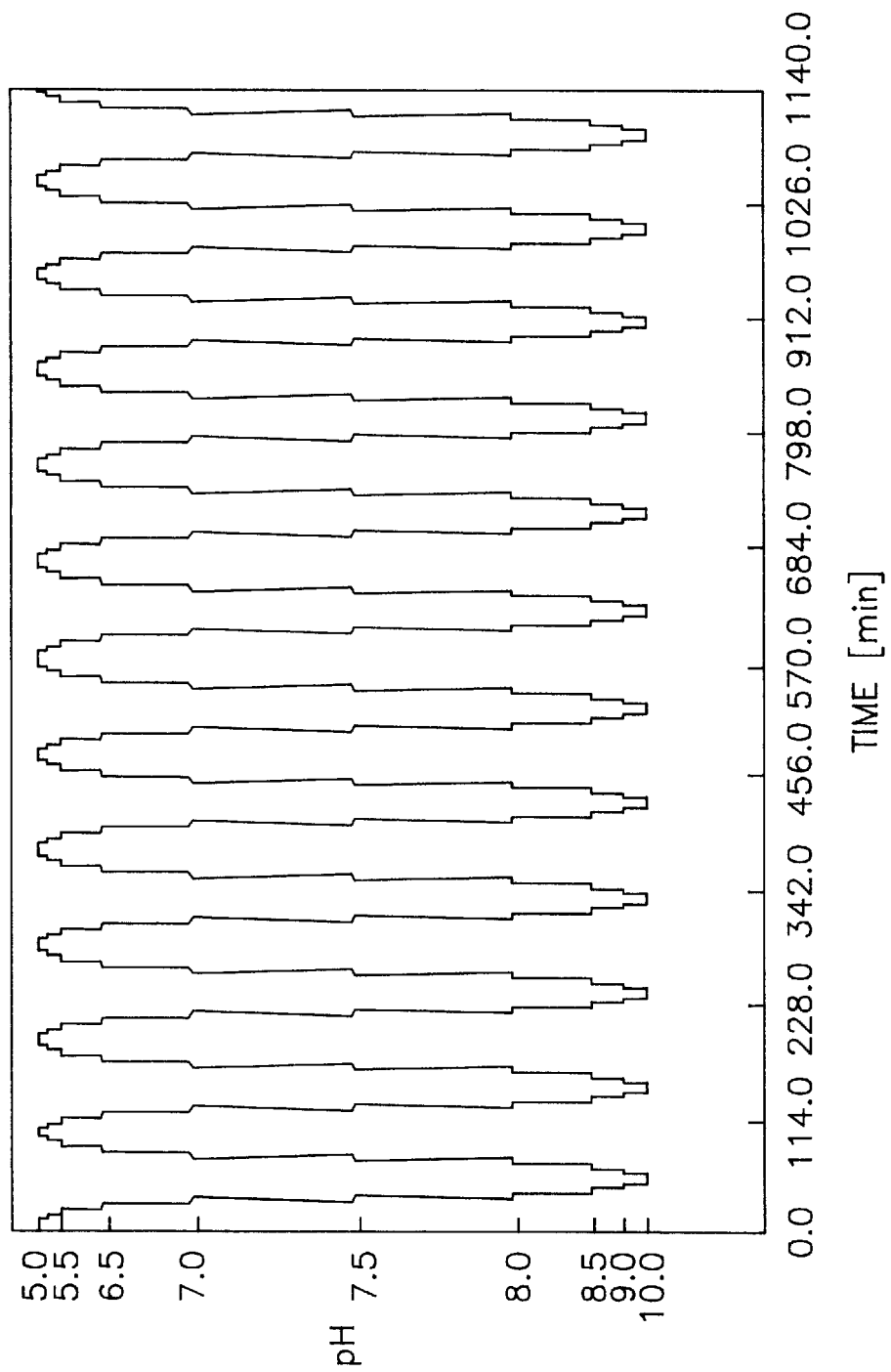

The invention is described below in more detail with reference to the diagrammatic drawings. FIG. 1 shows the layer structure of a planar optical pH-sensitive membrane in contact with the sample medium. The accommodating layer containing the indicator dye is attached to only one side. FIG. 2 shows the absorption spectra of the acid and alkaline form of a pH sensor membrane according to the invention (Example) and the FIGS. 3–5 show the pH-dependent absorption changes of the sensor membrane with various dye coatings. By selecting different dyes it is possible to set the pH range desired in each case. FIG. 6 shows a fiber-optic configuration comprising a light source, a light pipe, the sensor membrane at the tip, and a light pipe which passes the collected reflected light (or fluorescent light) to a photodetector. FIG. 7 shows the response of the sensor membrane according to the following example with respect to different values for the pH, and FIG. 8 shows a long-time test with a sensor membrane of this type.

FIG. 1 (not to scale) shows the cross section through an example of a sensor membrane S according to the invention. On a polyester membrane as the support element 1, with a typical thickness of approximately ®µm, there is a thin accommodating layer 2 made of cellulose, which is chemically dyed. Flowing over this membrane is the sample solution 3 which determines the color of the cellulose layer. The color can be scanned with the aid of corresponding opto-electronic configurations, inter alia with the aid of fiber-optic optical waveguides. In order to prevent ambient light from obstructing the measurement of the reflectivity or fluorescence of the membrane, the latter may alternatively be covered by a so-called optical insulation. To this end, the membrane is covered with a proton-permeable but optically opaque thin layer, for example with white-pigmented hydrogel.

FIG. 2 shows the absorption spectra of the sensor membranes obtained according to the example at acid (4.00) and alkaline (10.00) pH. It can be clearly seen that the absorption maximum of the alkaline form (II) at 595 nm is well matched to the emission wavelength of a yellow LED (590 nm) and can be readily measured with the aid thereof.

FIGS. 3 to 5 show the changes, measured at 565 nm, of the absorption intensities of various membranes which are obtained by immobilizing the compounds, used as an indicator dye, 2-[4-(2-hydroxy-7-sulfo-1-naphthylazo)-3-nitrophenylsulfonyl]ethyl hydrogen sulfate (FIG. 3), 2-[3 (4-anilinophenylazo)-4-carboxyphenylsulfonyl]ethyl hydrogen sulfate (FIG. 4) and 2-[3-(4-hydroxy-1-naphthylazo)-4-sulfophenylsulfonyl]ethyl hydogen [sic] sulfate (FIG. 5).

FIG. 6 shows a configuration for the fiber-optic measurement of the reflectivity of a sensor membrane according to the invention. Light from a light source L is launched into an optical waveguide LWL 1 and directed onto the sensor membrane S which is in contact with the sample. The light reflected by the membrane as a function of the pH is reabsorbed by the same fiber, and after passing a fiber coupler FK, is passed, via the optical waveguide LWL 2, to a photodetector D. The latter supplies a photocurrent which, in a preamplifier, is converted into a voltage and then passed to an amplifier unit, a digitized unit and finally an evaluation unit. This configuration makes it possible, in particular, to carry out on-line and remote measurements.

FIG. 7 shows the reflectivity measured with the aid of a fiber-optic photometer (corresponding to FIG. 6) of the sensor membrane obtained according to Example 1 at various values of the pH. The settling times throughout are in the range between 10 and 30 seconds, except for the transition from pH 8.02 to 8.97 where it is approximately 90 seconds.

FIG. 8 shows a long-time test over a 19 hour period on the sensor membrane, with a constant change between the following values for the pH: 5.00, 5.50, 6.00, 6.50, 7.00, 7.50, 8.00, 8.50, 9.00, 10.00, 9.00, 8.50, 8.00, 7.50, 7.00, 6.50, 6.00, 5.50 and 5.00. The sensor evidently has excellent long-term stability and good reproducibility.

The following example is intended to describe the fabrication of such a membrane according to a simple process, without however limiting the scope of the method to this specific process.

EXAMPLE

Fabrication of a rapidly responding pH sensor membrane 900 mg of 2-[4-(4-hydroxy-1-naphthylazo)-3-nitrophenylsulfonyl]-ethyl hydrogen sulfate are dissolved in 1.0 g of concentrated sulfuric acid by first comminuting the dye. The solution is then left to stand in a dry atmosphere for 30 minutes. It is then poured into 1000 ml of distilled water and neutralised with approximately 1.8 ml of 32%-strength aqueous sodium hydroxide until the color changes to green.

In this solution, a cellulose-coated polyester membrane (for example the product 17703T, commercially available per se from Hewlett-Packard, Vienna, as an overhead transparent foil which can be written on) is suspended and the solution is stirred slowly. After 5 minutes, 25 g of solid sodium carbonate are added and after a further 5 minutes, 5.2 ml of the 32%-strength aqueous sodium hydroxide. The mixture is left to stand for one more hour while being stirred. The now dyed membranes are washed with distilled water until the washwater remains colorless. The material obtained has a yellow color in acidic solutions and a blue color in alkaline solutions. The useful pH range is between 6 and 9.

The dyes mentioned can be immobilized by methods similar to the processes described in Angew. Chemie, 76, 423 (1964), which provides pH-sensitive membranes which change color in other pH ranges (of 8–11, 11–13 and 1–5).

The sensor membranes according to the invention are preferably used for determining pH with the aid of test strips using photometric or reflectometric evaluation, for determining the pH of very weakly buffered solutions (for example of surface water and rainwater) and in measuring physiological pH, optionally with the aid of fiber-optic optical waveguides.

I claim:

1. Sensor membrane for the reversible optical indication of the pH of a sample, having a mechanically stable support element and an indicator dye layer disposed thereon, which comprises a hydrophilic homogeneous, non-fibrous accommodating layer disposed on at least one side of the support element, which layer contains the indicator dye in an immobilized form.

2. Sensor membrane according to claim 1, wherein the accommodating layer has a thickness in the range from 0.1 to 0.5 µm.

3. Sensor membrane according to claim 1, wherein the accommodating layer comprises a component selected from the group consisting of cellulose, gelatine, hydrogel and hydrophilic polyvinyl alcohols.

4. Sensor membrane according to claim 1, characterized in that the support element comprises a hydrophobic, optically transparent material.

5. Process for fabricating a sensor membrane for reversible optical indication of the pH of a sample, in which a layer comprising indicator dye is applied onto a mechanically stable support element, wherein a hydrophilic homogeneous, non-fibrous accommodating layer is applied simultaneously with the indicator dye onto the support element, into which layer the indicator dye is introduced and immobilized.

6. Process according to claim 5, wherein hydrophobic, optically transparent material is used as the support element.

7. A method of using a sensor membrane according to claim 2 as a test strip for determining the pH in unbuffered or weakly buffered systems which comprises applying a sample to said sensor membrane and optically monitoring said sensor membrane.

8. Sensor membrane according to claim 4, characterized in that the optically transparent material is selected from the group consisting of polyesters of the phthalate type, polycarbonates, polyvinyl chlorides, polyamides, silicones, crosslinked polyacrylamides, and polyvinyl alcohols.

9. Process for fabricating a sensor membrane for reversible optical indication of the pH of the sample, in which a layer comprising indicator dye is applied onto a mechanically stable support element, wherein a hydrophilic accommodating layer is applied onto the support element following which an indicator dye is introduced into said accommodating layer and immobilized.

10. Process according to claim 9, wherein hydrophobic, optically transparent material is used as the support element.

\* \* \* \* \*